United States Patent [19]

Kust

[11] Patent Number: 5,073,190

[45] Date of Patent: Dec. 17, 1991

[54] SUBSTITUTED PHTHALIMIDO CYCLOHEXANECARBOXAMIDES AND COMPOSITIONS THEREOF FOR ENHANCING GROWTH OF HYBRID TEA ROSE PLANTS

[75] Inventor: Cyril A. Kust, Pennington, N.J.

[73] Assignee: American Cyanamid Company, Stamford, Conn.

[21] Appl. No.: 712,000

[22] Filed: Mar. 18, 1991

Related U.S. Application Data

[62] Division of Ser. No. 448,771, Dec. 11, 1989, Pat. No. 5,019,154.

[51] Int. Cl.$^5$ .................... A01N 43/38; C07D 209/34
[52] U.S. Cl. ..................................... 71/95; 548/477; 71/96
[58] Field of Search ............................. 71/95; 548/477

*Primary Examiner*—David B. Springer
*Attorney, Agent, or Firm*—Alice C. Brennan

[57] ABSTRACT

This disclosure describes a new compound 1-(3-chloro-4-methyl-phthalimido)-cyclohexanecarboxamide and the use of said compound and 1-(3-chlorophthalimido)-cyclohexanecarboxamide for enhancing axillary bud growth of hybrid tea rose plants.

3 Claims, No Drawings

SUBSTITUTED PHTHALIMIDO CYCLOHEXANECARBOXAMIDES AND COMPOSITIONS THEREOF FOR ENHANCING GROWTH OF HYBRID TEA ROSE PLANTS

This application is a division of application Ser. No. 07/448,771, filed Dec. 11, 1989, U.S. Pat. No. 5,019,154.

BACKGROUND OF THE INVENTION

1. Field of the Invention

The present invention relates to a novel compound 1-(3-chloro-4-methyl-phthalimido)- cyclohexanecarboxamide. The invention further relates to the unique method of using said compound and 1-(3-chlorophthalimido)-cyclohexanecarboxamide for enhancing axillary bud growth of hybrid tea rose plants.

2. Description of the Related Art

By way of background, U.S. Pat. Nos. 4,017,299 and 3,940,419 are cited. These patents describe phthalimido derivatives which are useful as plant growth regulants for certain crops. In particular, the compound 1-(3-chlorophthalimido)-cyclohexanecarboxamide is prepared. Although found within the broad, generic disclosure of the patents, the new compound 1-(3-chloro-4-methyl-phthalimido)-cyclohexanecarboxamide of the present selective invention is not specifically named, described or exemplified therein.

Additionally, the patents do not describe any of the phthalimido derivatives as possessing plant growth regulating properties for use on rose plants. Basically, it is well known that the response of rose plants to exogenous treatment is highly species specific and, at times, even varietal dependent as well. For example, the compound 2-chloroethyltrimethylammonium chloride is used commercially to improve the quality of some varieties of azalea plants, yet is ineffective on other varieties of azaleas and roses. Another example is gibberellic acid which is recommended for commercial application on many crops including ornamental crops such as pompom chrysanthemums and statice. But, gibberellic acid has no effect on other types of chrysanthemums or on roses. Hence, a compound's ability to regulate growth in crops does not suggest or predict the compound's ability to enhance axillary bud growth in rose plants.

SUMMARY OF THE INVENTION

It is therefore an important object of the present invention to provide substituted phthalimido cyclohexanecarboxamide compounds which are useful for regulating the growth of hybrid tea rose plants.

Another object is to provide a new phthalimido cyclohexanecarboxamide compound which is useful in a method for enhancing axillary bud growth of a hybrid tea rose stem.

A further object is to provide a unique method for enhancing axillary bud growth of a hybrid tea rose stem which increases the quality and the number of cut stems of roses.

Further purposes and objects of the present invention will appear as the specification proceeds.

With the foregoing and other objects in view, the invention herein provides a novel compound 1-(3-chloro-4-methyl-phthalimido)-cyclohexanecarboxamide and a unique method of utilizing said compound or the known compound 1-(3-chlorophthalimido)-cyclohexanecarboxamide for enhancing axillary bud growth of a hybrid tea rose stem. The background of the invention and its departure from the art will be further described hereinbelow.

DETAILED DESCRIPTION OF THE INVENTION

The present invention pertains to a novel method for uniquely regulating the growth of hybrid tea rose plants by the application of certain substituted phthalimido cyclohexanecarboxamide compounds. Surprisingly, these compounds are able to increase the quality and the number of the cut stems of roses produced per rose plant. This invention further relates to a new 1-(3-chloro-4-methyl-phthalimido)-cyclohexanecarboxamide which has the structure:

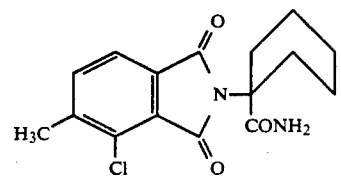

Generally, the compounds of this invention may be prepared by any conventional processes within the art. By way of illustration, U.S. Pat. No. 3,940,419 (incorporated herein by reference thereto) describes a method of preparation of the known compound 1-(3-chlorophthalimido)-cyclohexanecarboxamide (see, e.g., Examples 22–24, cols. 26–27). The new compound of this invention, 1-(3-chloro-4-methyl-phthalimido)-cyclohexanecarboxamide, may be made by the process graphically shown in Flow Diagrams A and B. In Flow Diagram A, the compound (IV), 3-chloro-4-methylphthalic anhydride, is obtained via the ortho-directed metallation of 3-chloro-4-methylbenzamide (II) by treatment with sec-butyl lithium in an anhydrous non-protic solvent such as tetrahydrofuran in the presence of N,N,N',N'-tetramethylethylenediamine (TMEDA). The metallation is followed by carboxylation to give 3-chloro-4-methylphthalic acid (III). The corresponding anhydride (IV) is obtained by reaction with acetic anhydride. U.S. Pat. No. 4,554,013 (incorporated herein by reference thereto) describes the sequence of reactions to obtain the anhydride (IV) in further detail (see, e.g., Examples 1–3, cols. 20–22). This sequence is graphically illustrated below in Flow Diagram A.

FLOW DIAGRAM A

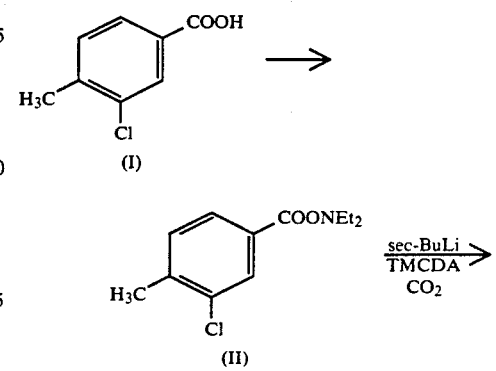

-continued

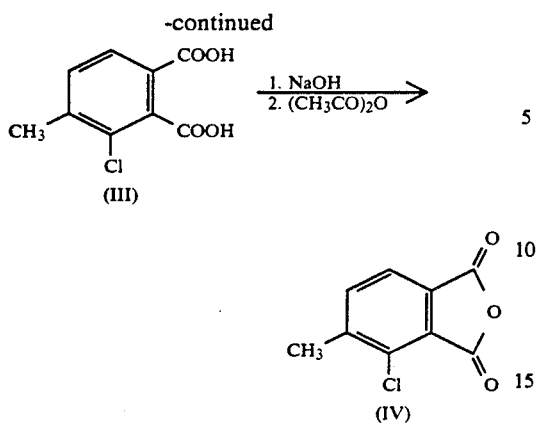

In Flow Diagram B, the above-obtained 3-chloro-4-methylphthalic anhydride is sequentially reacted with spirocyclohexylaminonitrile (VI) and acetic anhydride to yield the desired 3-chloro-4-methylphthalimide nitrile (VIII) which can be hydrolyzed in the presence of sulfuric acid to give the corresponding phthalimido-carboxamide (IX). The spirocyclohexylaminonitrile is readily obtained from cyclohexanone (V) via the Strecker synthesis. This sequence of reactions is illustrated below.

FLOW DIAGRAM B

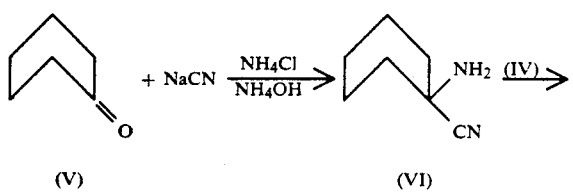

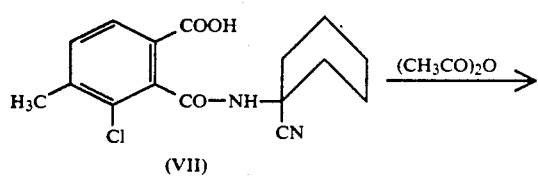

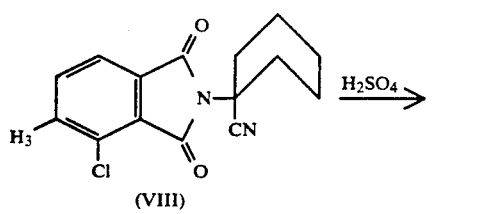

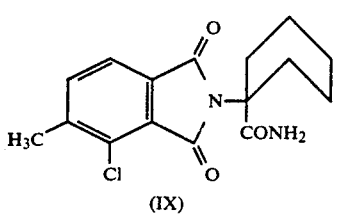

Using essentially the same procedure and substituting 3-chlorophthalic anhydride (X) for compound IV, 1-(3-chlorophthalimido)-cyclohexanecarboxamide (XII) is obtained as shown in Flow Diagram C.

FLOW DIAGRAM C

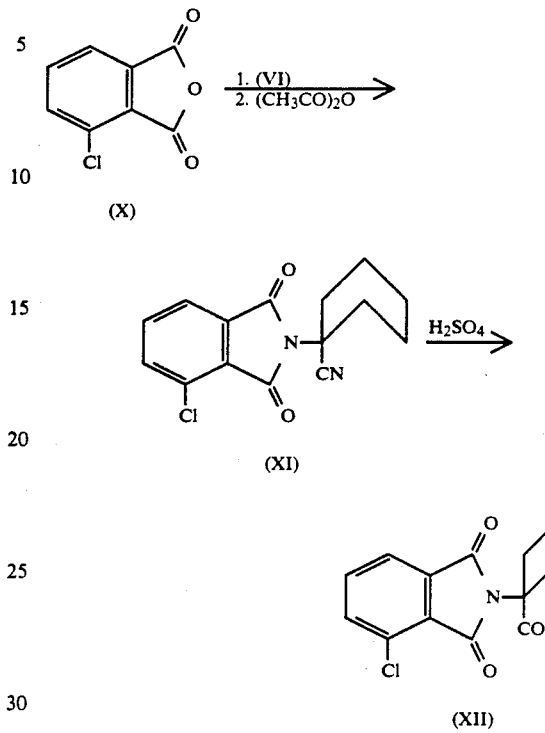

Although 1-(3-chloro-4-methyl-phthalimido)-cyclohexane-carboxamide is the preferred new compound of the present invention, it is contemplated that other halogens such as bromine may be used in lieu of chlorine. Also, ethyl and butyl may substitute for the methyl.

The active compounds of the present invention are useful for selectively regulating the growth of hybrid tea rose plants. In particular, the invention relates to a unique method for enhancing axillary bud growth of a hybrid tea rose stem which comprises applying to the roots, stems or foliage of a hybrid tea rose plant or to the soil in which the plant is grown, an effective growth regulating amount or, more specifically, an effective axillary bud growth enhancing amount of the substituted phthalimido cyclohexanecarboxamide compounds described herein. Preferably, the new compound 1-(3-chloro-4-methyl-phthalimido)-cyclohexanecarboxamide is applied as a soil drench after plant establishment. For the unique application to enhance the growth of a rose plant, the known compound 1-(3-chlorophthalimido)-cyclohexanecarboxamide is desirably incorporated into a solution which is sprayed directly on the foliage and stems of the rose plant, i.e., by foliar application. Alternatively, this compound may be applied as a preplanting bare-root soak or as a soil drench during the growing period after plant establishment.

The effective amount useful in the practice of this invention ranges, insofar as the new compound is concerned, from about 0.10 mg ai per plant to 60 mg ai per plant, and preferably from about 4.0 mg ai per plant to 24 mg ai per plant. The effective amount of 1-(3-chlorophthalimido)-cyclohexanecarboxamide ranges from about 0.02 mg ai per plant (i.e., about 1.0 g ai on an acre-planted basis) to 1.0 mg ai per plant, and desirably from about 0.04 mg ai per plant to 0.3 mg ai per plant. Examples of the hybrid tea rose plants include, but are not limited to, *Rosa hybrida* var. Samantha and Royalty.

Desirably, the advantage of the substituted phthalimido cyclohexanecarboxamide compounds of this invention lies in possessing the unexpected property of being able to enhance axillary bud growth. Applying the compounds to the hybrid tea rose plants beneficially increases the quality and the number of cut stems of roses. Basically, the effect increases the overall number of commercially acceptable roses produced per rose plant. Such effect is surprisingly achieved by the breaking of axillary bud dormancy in the next harvest cycle following treatment. However, other advantages may readily become apparent to the skilled artisan based upon the disclosure herein. For example, the compounds may also be useful for uniquely controlling stem lengths of cut roses in commercial operations. Additionally, both compounds may find use in increasing new root and stem growth of newly-planted hybrid tea rose varieties and miniature rose varieties.

By way of illustration, the below Examples 5-8 demonstrate the novel properties of the compounds of this invention in promoting the growth and quality of hybrid tea rose plants. Surprisingly, the novel compound of the present invention substantially increases stem yields even though it is at the time of year when stem yields from control plants show a seasonal decrease. And, also surprisingly, very beneficial effects are obtained in roses at a rate of application of 1-(3-chlorophthalimido)-cyclohexanecarboxamide to the foliage of less than 4.0 g ai/acre (25 ppm spray solution), whereas U.S. Pat. Nos. 4,017,299 and 3,940,419 teach that the compound is effective to other crop plants when applied within the range of 0.06 lb ai/acre (27.2g) to 32 lb ai/acre.

The present invention further deals with novel compositions for regulating the growth of the hybrid tea rose plants comprising the effective growth regulating amount of the active ingredient in conjunction with an inert carrier. The amount of the active ingredient will be contingent upon the type of application, the selection of carrier and the intended results. The carrier may be a solid or a liquid. Selection of the carrier involves considering such usual factors like compatibility with the active ingredient, lack of phytotoxicity in use with the rose plant, method of application, time of application, etc. Due to the low water solubility of the compounds of the invention, other factors which are within the formulation art will need to be taken into consideration. Obviously, the rose plant has certain requirements such as sufficient water and absorption of the compound in ionic form. Nevertheless, any convenient carrier that assures the compound will be uniformly applied and adequately absorbed by the plants will suffice. The carrier will further vary depending upon the type of application and the desired results. For example, it may be desirable to add surfactants, preferably anionic surfactants such as Aerosol OT ® (sodium dioctyl sulfosuccinate, commercially available from American Cyanamid Company), Igepon T77 ® (sodium-N-methyl-N-oleoyl taurate, commercially available from GAF Chemicals Corporation), Morwet EFW ® Powder (sulfated alkyl carboxylate and sulfonated alkyl naphthalene, sodium salt, commercially available from Desoto, Inc.), and the like, if the formulation will be needed for foliar application. Alternatively, no surfactant may be necessary if the active compound will be applied as a soil drench or as a bare root soak. Under that circumstance, the active compound may be mixed simply with dimethyl formamide or an acetone-water mixture, typically 40:60 or 50:50 ratio amounts of acetone to water, in sufficient quantity to dissolve the compound.

Typical formulations which are useful in the practice of the present invention include, but are not limited to, wettable powders, dusts, granular formulations, soil drenches, etc.

Wettable powders can be prepared by blending the active compound with a solid carrier, such as attapulgite, kaolin, diatomaceous earth, silica and the like, and small amounts of dispersants and wetting agents and air-milling the blended mixture to effect reduction of particle size to about the 5 to 10 micron range. A typical wettable powder might contain 20% by weight of the active ingredient, 5% by weight of a highly purified partially desulfonated sodium lignin sulfonate, 1% by weight of sodium N-methyl-N-oleoyltaurate and 74% by weight of attapulgite.

In practice, it will also be found that the active ingredient in the formulation can be varied from about 5.0% to 50.0% by weight. In such cases, the solid diluent will have to be varied accordingly.

For the preparation of a dust, for example, a 2.0% dust, 10.0% by weight of the 20.0% wettable powder can be blended with about 90.0% by weight of a solid carrier, such as kaolin. Suitable equipment for such preparations are ribbon-type blenders and double-cone blenders. The concentration of active ingredient in dust formulations can be readily varied by adjusting the amount of wettable powder and carrier used. Typical dusts will generally vary between about 0.10% to 5.0% by weight of active ingredient, although higher concentrations may also be prepared.

An alternative process for preparation of dusts involves blending the active compound with the solid carrier and passing the uniform blend through an attrition mill to obtain the desired particle size.

Typical granular formulations can be readily prepared using conventional materials and procedures common to the art. It is, of course, obvious that the amount of active ingredient in the formulated granular product can be widely varied, preferably between about 0.10% to 10.0% ai by weight. This simply requires appropriate adjustment of the amount of granular carrier used and/or adjuvants added. Sorptive granular carriers, as well as non-sorptive carriers, can be employed in the preparation of the granular formulation.

The appropriate formulation may be applied to the root system, directly to the stems or to the foliage of the hybrid tea rose plant. Alternatively, the formulation may be applied to the soil in which the plant is grown.

A further understanding of the present invention can be obtained from the following examples. However, the examples are set forth only for the illustration of certain aspects of the invention and are not to be construed as limitations thereon. Unless otherwise noted, all parts are by weight. The amount of moles or millimoles ("mol" or "mmol") refers to the molar equivalent of each reactant used in the reaction mixtures of the examples.

EXAMPLE 1

Preparation of α-Aminocyclohexanecarbonitrile

A rapidly stirred mixture of about 200 ml ammonium hydroxide (reagent grade), about 61.2 g (1.25 mol) of sodium cyanide and about 53.5 g (1.5 mol) of ammonium chloride at 10° C. is treated with about 98.3 g (1.0 mol) of cyclohexanone in a steady stream; exotherm to about 40° C. with bubbling (release of NH₃ is observed). After 45 minutes at 38° C. and 16 hours at ambient temperatures, stirring is discontinued and the reaction mixture is diluted with about 100 ml water and about 500 ml diethyl ether and then shaken vigorously. The phases are separated. The organic phase is dried over magnesium sulfate and concentrated in vacuo at 28° C. to 30° C. to afford the title compound as a cloudy colorless oil, 110.1 g (88.7% yield), identified by infrared, NMR and mass spectral analysis.

EXAMPLE 2

Preparation of 2-[(1-Cyano-2-cyclohexyl)carbamoyl]-3-chloro-4-methylbenzoic Acid The compound 3-chloro-4-methylphthalic anhydride is prepared by the process described in Examples 1-3, cols. 20-22, of U.S. Pat. No. 4,554,013 (incorporated herein by reference thereto). A solution of about 15.8 g (0.08 mol) of 3-chloro-4-methylphthalic anhydride in about 300 ml dry tetrahydrofuran is treated with about 10.9 g (0.088 mol) of spirocyclohexylaminonitrile and about 11.2 ml (0.08 mol) of triethylamine, stirred for 16 hours at room temperature and concentrated in vacuo to give a residue. The residue is dispersed in about 200 ml methylene chloride and about 200 ml of 0.5N sodium hydroxide. The phases are separated and the aqueous phase is cooled to 10° C. and carefully acidified to pH 2 with concentrated sulfuric acid. The resultant acidic, aqueous mixture is diluted with about 700 ml ethyl acetate and filtered. The filtrate is separated and the organic phase is concentrated in vacuo to give the title compound as a white solid, 15.3 g, identified by infrared, NMR and mass spectral analysis.

EXAMPLE 3

Preparation of 3-Chloro-N-(1-cyanocyclohexyl)-4-methylphthalimide

A stirred mixture of about 15.3 g (0.05 mol) of 2-[(1-cyano-2-cyclohexyl)carbamoyl]-3-chloro-4-methylbenzoic acid in about 250 ml acetic anhydride is heated at reflux temperature for 4 hours, allowed to come to room temperature over a 16 hour period and filtered. The filter cake is washed with a small amount of toluene and dried in vacuo at 53° C. for about 2 hours to give the title compound as a white crystalline solid, 6.5 g (45% yield), mp 165° C.–168° C., identified by infrared, NMR, mass spectral and elemental analysis.

EXAMPLE 4

Preparation of 1-(3-Chloro-4-methyl-phthalimido)-cyclohexanecarboxamide

A solution of about 4.35 g (14.4 mmol) of 3-chloro-N-(1-cyanocyclohexyl)-4-methylphthalimide in about 50 ml methylene chloride is added to concentrated sulfuric acid and water at less than 10° C. with rapid stirring. The reaction mixture is stirred very vigorously at ambient temperatures for 4 hours (reaction complete by thin layer chromatography), poured over crushed ice and extracted with about 450 ml methylene chloride. The organic extracts are combined and concentrated in vacuo to give a white fluffy precipitate. The precipitate is filtered and air dried to give the title product, 2.86 g (62% yield), mp 192° C.–208° C., identified by infrared and NMR analysis.

EXAMPLE 5

Effects of 1-(3-Chlorophthalimido)-cyclohexanecarboxamide for Enhancing the Growth of Hybrid Tea Rose Plants Samantha variety hybrid tea rose bare-root plants are obtained from Jackson-Perkins Company, Medford, Ore. The plants are kept moistened and stored in the shipping boxes in a cold room (4° C.) until they are made ready for planting. Following directions of commercial growers, the plants in the original shipping boxes are moved into the greenhouse (day air temperature of 25° C. to 32° C., night air temperature of 15° C. to 20° C.) for two days. At this time, new root growth is visible. Most of the plants are now set in 3-gallon black plastic tubs (10 inches wide by 9 inches deep). The conventional planting medium consists of 3 parts Terralite ® Metro-Mix Growing Medium 350 (a mineral growth medium commercially available from W. R. Grace & Co., Cambridge, Mass.) and 1 part greenhouse soil (⅓ washed mason sand, ⅓ silt loam soil and ⅓ sandy loam soil). The tubs are filled to within inch of the top with the planting medium. The tubs are watered to saturation with a nutrient solution of Peter's Professional Water Soluble Fertilizer ® 20-10-20 N/P/K (also commercially available from W. R. Grace & Co.) and are allowed to drain to field moisture capacity. The tubs are set in a greenhouse under normal conditions as described above.

After new root growth is visible, eight of the plants are placed in a container deep enough to allow total immersion of the roots in water. An amount of a water-based formulation containing 240 g of active ingredient per liter, sufficient to maintain the saturation amount of the active ingredient in solution during the course of the bareroot soak procedure, is added to the water. (The water solubility of 1-(3-chlorophthalimido)-cyclohexanecarboxamide is about 30 ppm at 25° C.) The roots are allowed to absorb the active ingredient for about 18 hours and are then planted as described above.

Throughout the duration of the study, the plants are watered, as needed, with a solution of the 20-10-20 N/P/K Peters' Professional Water Soluble Fertilizer ®, or with a solution of other analyses of N/P/K, or with water only. Minor elements are supplied, as needed, by the use of Peter's Soluble Trace Elements Minerals (S.T.E.M.) ® fertilizer solution (commercially available from W. R. Grace & Co). During the course of the study, the photoperiod is maintained at least 16 hours by applying supplemental lighting with metal halide lamps or with other suitable artificial lighting systems.

When each new stem reaches the stage of growth of 'flower bud visible,' the stem is pinched back to just above the second 5-leaflet leaf. Theoretically, new stems will grow from the axillary buds of the first and second 5-leaflet leaves. That is the commercial practice to increase stem number and, thereby, cut flower production of the plants. After the pinchback, the growth is allowed to proceed to the production of flowers for the cut stem rose market.

Regrowth of the plants after the stem pinchback is the stage of 'color visible' in the buds of the most advanced stems. On that day, three types of treatments of 1-(3-chlorophthalimido)-cyclohexanecarboxamide are applied to four or eight plants per treatment.

For foliar applications, spray solutions are prepared by using appropriate amounts of a water-based formulation, which contains 240 g of active ingredient per liter, to give final solutions that contain 50 or 100 mg of active ingredient per liter of water. After the formulation is dispersed in the water, an anionic surfactant, Aerosol OT® 70%, is added to the water to a final concentration of about 0.05% to 0.25% v/v of the final spray solution. The surfactant increases absorption of the active ingredient by the leaf and stem tissues of the rose plants. The solution is applied to either four or eight plants with a standard compressed air sprayer that delivers a volume of about 60 gallons per acre on a surface area basis. Since the plants have not established a closed leaf canopy and are grown in 10-inch diameter pots spaced at one foot between plants, much of the spray falls between the leaves and between the pots and is not available for absorption by the rose foliage and stems.

Eight of the plants are treated with a soil drench of the active ingredient. The drench is prepared by mixing 1.53 ml of a 240 g ai/L water-based formulation of 1-(3-chlorophthalimido)-cyclohexanecarboxamide with water to a final volume of 8.0 liters. One liter of the solution is applied to the surface of the soil in each of eight pots containing a Samantha rose plant. The rate of application is 8.0 lb ai/acre on a surface area basis (46 mg ai/pot). Based on the commercial practice of allowing one square foot of bed space per plant, the rate is 4.42 lb ai/acre on an individual plant basis.

After application of the treatments and continued growth of the plants, rose stems are harvested by the standard method used in commercial operations. Each stem is cut back to either above the first or above the second 5-leaflet leaf, dependent on whether the diameter of the stem is or is not sufficient to support the weight of two potential new stems that might develop from the axillary buds of the 5-leaflet leaves. Each stem is measured and the number of stems and length in inches per stem from each plant is recorded.

It can be seen from Table I that, whether applied as a bare-root soak before planting or as foliar sprays after regrowth following a stem pinchback, the compound 1-(3-chlorophthalimido)-cyclohexanecarboxamide surprisingly increases the number of stems produced by the plants in the first harvest.

The rose plants are grown through four more harvest cycles. In the first and second harvest cycles, very high outside air temperatures result in greenhouse temperatures that often exceed 35° C. Plants are unable to absorb enough water to compensate for high transpirational losses. Under such high stress conditions, the flower quality of cut roses is so poor that no meaningful data are obtained regarding effect of treatment with the active ingredient on improving quality of the cut stems. However, conditions during cooler weather are favorable for rose plant growth in the third, fourth and fifth harvests. In those harvests, each stem is measured and evaluated for acceptable quality for the commercial market.

Cut stems are discarded if the stem is weak, bent or too short, if the head is too small or bent at the attachment to the peduncle, or if the head is misshapen ("bull head"). It can be seen from Table II that the average percent of acceptable commercial rose stems in each of the third through fifth harvests is increased greatly by each treatment with the active ingredient.

EXAMPLE 6

Effects of Foliar Application of 1-(3-Chlorophthalimido)-cyclohexanecarboxamide on Red Hybrid Tea Rose Plants Concentrations of 25 ppm and 100 ppm of 1-(3-chlorophthalimido)-cyclohexanecarboxamide (as a water-based formulation that contains 240 g ai/L of active ingredient) plus 0.10% v/v Aerosol OT® 70% anionic surfactant are applied to the foliage and stems of Royalty variety red hybrid tea rose grown in a commercial greenhouse (Wright's Roses, Cranbury, N.J.) for production of cut stems. Each treatment is applied to a set of 80 Royalty plants. The stage of growth of the stems ranges from stems that are just beginning growth to stems that have flower buds in the first color stage.

The plants are subject to all normal management cultural practices used in the commercial greenhouse. After about four days to five weeks, the stems are harvested. The length of each stem is recorded and stem quality is judged as described in Example 5. It can be seen from Table III that there is a surprising increase in the percent of commercially acceptable cut stems produced by the Royalty rose plants treated with 1-(3-chlorophthalimido)-cyclohexane-carboxamide as foliar applications.

EXAMPLE 7

Effects of Foliar Application of 1-(3-Chlorophthalimido)-cyclohexanecarboxamide on Red Hybrid Tea Rose Plants Five sets of 96 Royalty red hybrid tea rose plants located in a commercial greenhouse (Wright's Roses, Cranbury, N.J.) under standard greenhouse conditions are marked off with colored tapes for identification of the five sets of plants. Stems are harvested, the stems are measured for length and the quality of each stem is judged. The data are kept separate for each set of 96 plants. These data provide a base level of number and quality of the stems produced by the plants in each set.

Treatment positions are assigned at random among the five sets of plants. Treatments consist of untreated control plants, and plants treated with water spray solutions containing either 25, 50, 100, or 200 ppm of 1-(3-chlorophthalimido)-cyclohexanecarboxamide (sourced from a waterbased formulation containing 240 g ai/L of active ingredient). An anionic surfactant, Aerosol OT® 70%, is added to each solution to a final concentration of 0.20% ai on a v/v basis. Each solution is applied at a spray volume of 40 gallons of water at 30 psi air pressure as fine sprays to the foliage and stems of the rose plants. At the spray volume used, the rates of application per acre on a surface area basis are 4.0, 8.0, 16.0 and 32.0 g ai/acre. Since much of the spray solution is not deposited on rose foliage or stems, the rate of application to the rose plants is considerably lower than that on a surface area basis. At the time of application, the stage of growth of the rose stems ranges from stems about one inch long to stems up to 15 inches long with flower buds visible.

The stems are harvested from about five days to a month after the day of application. Stem length is measured and recorded, and stem quality is judged as described in Example 5. It can be seen from Table IV that each treatment of the active ingredient surprisingly increases stem quality and thereby increases the percent of stems that are acceptable for the wholesale cut stem market.

EXAMPLE 8

Effects of 1-(3-Chloro-4-methylphthalimido)-cyclohexanecarboxamide for Enhancing the Growth of Hybrid Tea Rose Plants Samantha variety hybrid tea rose plants are obtained from Jackson-Perkins Company, Medford, Ore. A soil drench of the compound 1-(3-chloro-4-methylphthalimido)-cyclohexane-carboxamide is prepared by mixing 1.53 ml of a 2.0 lb. ai/gal formulation of the compound with 8000 ml of water until the compound is dispersed. One liter of the solution is applied to each of eight rose plants as a soil drench. The rates of application are 4.0, 8.0 and 16.0 lb ai/acre on a surface area basis.

Three treatments are applied during the first to third harvests. At each harvest, each stem is measured and records are kept of the number of stems harvested within the length ranges of <14 inches, 14 to 18 inches, 18 to 22 inches, 22 to 26 inches, and >26 inches. The stem harvest during the period encompassing the date of application of the compound is considered to be the base productivity level of the plants for that production period. The effect of the active compound is expressed in the number of stems obtained in the next harvest, since the axillary buds of the first and second 5-leaflet usually will not begin growth until the apical dominance of the flower is eliminated by the harvest of the stem.

Surprisingly, the novel compound of the present invention increases stem yields in the subsequent harvest at a time in the year during which stem yields from control plants are showing a seasonal decrease. Equally surprisingly, there is a linear 40% increase in the numbers of stems as the rate of application of the compound is doubled. Examination of the data of stem length distribution shows that as the rate of application of the compound is increased, there are more stems in the shorter stem categories.

The data are reported in below Table V.

TABLE I

SAMANTHA HYBRID TEA ROSES - CUT STEM HARVEST DATA

| TREATMENT | NUMBER OF PLANTS | HARVEST NUMBER | NUMBER OF STEMS HARVESTED-PER STEM LENGTH IN INCHES | | | | | TOTAL STEMS | AVE. STEM LENGTH INCHES | AVE. NO. STEMS PER PLANT |
|---|---|---|---|---|---|---|---|---|---|---|
| | | | <14 | 14-18 | 18-22 | 22-26 | >26 | | | |
| ROOT SOAK IN 30 PPM FOR 18 HOURS BEFORE PLANTING | 8 | 1st | 12 | 22 | 25 | 9 | 4 | 72 | 17.7 | 9.0 |
| | 8 | 2nd | 1 | 16 | 27 | 29 | 7 | 80 | 21.0 | 10.0 |
| | 8 | 3rd | 0 | 0 | 12 | 25 | 13 | 50 | 24.0 | 6.2 |
| | 8 | 4th | 0 | 0 | 8 | 12 | 19 | 39 | 25.8 | 4.9 |
| | 8 | 5th | 0 | 7 | 10 | 17 | 12 | 46 | 22.8 | 5.8 |
| | TOTALS OF 5 | | 13 | 45 | 82 | 92 | 55 | 287 | | 35.9 |
| 50 PPM FOLIAR AT 1st COLOR AFTER 1st PINCH | 4 | 1st | 7 | 12 | 6 | 5 | 0 | 30 | 16.4 | 7.5 |
| | 4 | 2nd | 3 | 7 | 11 | 11 | 0 | 32 | 19.0 | 8.0 |
| | 4 | 3rd | 0 | 0 | 5 | 6 | 9 | 20 | 24.8 | 5.0 |
| | 4 | 4th | 0 | 0 | 2 | 1 | 12 | 15 | 27.7 | 3.8 |
| | 4 | 5th | 1 | 3 | 3 | 7 | 6 | 20 | 23.2 | 5.0 |
| | TOTALS OF 5 | | 11 | 22 | 27 | 30 | 27 | 117 | | 29.3 |
| 100 PPM FOLIAR AT 1st COLOR AFTER 1st PINCH | 8 | 1st | 13 | 23 | 25 | 7 | 0 | 68 | 16.6 | 8.5 |
| | 8 | 2nd | 8 | 14 | 28 | 17 | 7 | 74 | 19.6 | 9.2 |
| | 8 | 2rd | 1 | 5 | 10 | 14 | 19 | 49 | 24.3 | 6.1 |
| | 8 | 4th | 0 | 0 | 4 | 1 | 24 | 29 | 28.4 | 3.6 |
| | 8 | 5th | 0 | 1 | 7 | 11 | 16 | 35 | 25.0 | 4.4 |
| | TOTALS OF 5 | | 22 | 43 | 74 | 51 | 66 | 255 | | 31.8 |
| 8.0 LB/A AS SOIL DRENCH AT 1st COLOR | 8 | 1st | 13 | 18 | 28 | 2 | 0 | 61 | 16.4 | 7.6 |
| | 8 | 2nd | 4 | 11 | 21 | 19 | 4 | 59 | 20.2 | 7.4 |
| | 8 | 3rd | 2 | 1 | 8 | 19 | 16 | 46 | 24.3 | 5.8 |
| | 8 | 4th | 0 | 1 | 4 | 12 | 18 | 35 | 26.0 | 4.4 |
| | 8 | 5th | 0 | 5 | 6 | 16 | 12 | 39 | 23.9 | 4.9 |
| | TOTALS OF 5 | | 19 | 36 | 67 | 68 | 50 | 240 | | 30.1 |
| CONTROL PLANTS | 8 | 1st | 6 | 15 | 24 | 8 | 1 | 54 | 18.1 | 6.8 |
| | 8 | 2nd | 1 | 19 | 27 | 15 | 7 | 69 | 20.0 | 8.6 |
| | 8 | 3rd | 1 | 3 | 6 | 18 | 19 | 48 | 24.4 | 6.0 |
| | 8 | 4th | 0 | 0 | 2 | 7 | 29 | 38 | 27.0 | 4.8 |
| | 8 | 5th | 0 | 1 | 4 | 10 | 15 | 30 | 24.9 | 3.8 |
| | TOTALS OF 5 | | 8 | 38 | 62 | 58 | 71 | 239 | | 30.0 |

TABLE II

SAMANTHA HYBRID TEA ROSES PERCENT COMMERCIAL STEMS

| TREATMENT | THIRD HARVEST | FOURTH HARVEST | FIFTH HARVEST | AVERAGE |
|---|---|---|---|---|
| ROOT SOAK IN 30 PPM FOR 18 HOURS PREPLANT | 74 | 87 | 96 | 86 |
| 50 PPM FOLIAR AT 1st COLOR AFTER 1st PINCH | 90 | 93 | 100 | 94 |
| 100 PPM FOLIAR AT 1st COLOR AFTER 1st PINCH | 76 | 93 | 97 | 89 |
| 8.0 LB AI/A AS SOIL DRENCH AT 1st COLOR | 80 | 91 | 97 | 89 |

TABLE II-continued
SAMANTHA HYBRID TEA ROSES
PERCENT COMMERCIAL STEMS

| TREATMENT | THIRD HARVEST | FOURTH HARVEST | FIFTH HARVEST | AVERAGE |
|---|---|---|---|---|
| CONTROL PLANTS | 71 | 82 | 80 | 78 |

TABLE III
ROYALTY RED HYBRID TEA ROSES-HARVEST DATA

| Stem Length Range-Inches | Control | 25 PPM | 100 PPM |
|---|---|---|---|
| NUMBER COMMERCIALLY ACCEPTABLE | | | |
| <14 | 0 | 7 | 1 |
| 14 to 18 | 21 | 30 | 24 |
| 18 to 22 | 55 | 64 | 61 |
| 22 to 26 | 25 | 32 | 28 |
| >26 | 3 | 6 | 7 |
| TOTAL | 104 | 148 | 121 |
| PERCENT | 58 | (+9%) 67 | (+7%) 65 |
| NUMBER COMMERCIALLY UNACCEPTABLE | | | |
| <14 | 2 | 9 | 3 |
| 14 to 18 | 23 | 28 | 8 |
| 18 to 22 | 38 | 32 | 42 |
| 22 to 26 | 12 | 3 | 11 |
| >26 | 1 | 0 | 0 |
| TOTAL | 76 | 72 | 64 |
| PERCENT | 42 | 33 | 34 |

TABLE IV
ROYALTY ROSES
STEM LENGTH CATEGORY AND PERCENT COMMERCIAL

| Wholesale Value/Stem in Cents | 70 <14" No. | %C | 70 14-18" No. | %C | 90 18—22" No. | %C | 119 22-26" No. | %C | 135 >26" No. | %C | Total No. | No. Comm. | Inc. in No. Comm. | % Inc. in Comm. |
|---|---|---|---|---|---|---|---|---|---|---|---|---|---|---|
| Control | | | | | | | | | | | | | | |
| Base Yield | 37 | 54 | 133 | 84 | 87 | 90 | 21 | 90 | 5 | 100 | 284 | 235 | 14 | 6.0 |
| 1st Harvest | 97 | 49 | 208 | 65 | 65 | 85 | 11 | 91 | 1 | 100 | 382 | 249 | | |
| % of Total Comm. | | 19 | | 54 | | 22 | | 4 | | .04 | | | | |
| 25 PPM | | | | | | | | | | | | | | |
| Base Yield | 14 | 50 | 120 | 80 | 92 | 93 | 29 | 100 | 2 | 100 | 257 | 220 | 28 | 12.7 |
| 1st Harvest | 84 | 48 | 208 | 68 | 69 | 81 | 10 | 100 | 0 | — | 371 | 248 | | |
| % of Total Comm. | | 16 | | 57 | | 23 | | 4 | | 0 | | | | |
| 50 PPM | | | | | | | | | | | | | | |
| Base Yield | 29 | 52 | 127 | 72 | 130 | 91 | 40 | 98 | 5 | 100 | 331 | 268 | 43 | 16.0 |
| 1st Harvest | 107 | 58 | 234 | 71 | 87 | 82 | 12 | 92 | 1 | 100 | 441 | 311 | | |
| % of Total Comm. | | 20 | | 53 | | 23 | | 4 | | .03 | | | | |
| 100 PPM | | | | | | | | | | | | | | |
| Base Yield | 49 | 55 | 164 | 83 | 93 | 96 | 18 | 100 | 3 | 67 | 327 | 272 | 30 | 11.0 |
| 1st Harvest | 102 | 46 | 233 | 74 | 84 | 86 | 10 | 80 | 0 | — | 432 | 302 | | |
| % of Total Comm. | | 16 | | 57 | | 24 | | 3 | | 0 | | | | |
| 200 PPM | | | | | | | | | | | | | | |
| Base Yield | 24 | 42 | 156 | 85 | 93 | 94 | 30 | 97 | 4 | 75 | 307 | 261 | 37 | 14.2 |
| 1st Harvest | 80 | 51 | 234 | 67 | 107 | 83 | 14 | 71 | 1 | 100 | 436 | 298 | | |
| % of Total Comm. | | 14 | | 53 | | 30 | | 3 | | .03 | | | | |

TABLE V
SAMANTHA TEA ROSES - HARVEST DATA

| COMPOUND RATE LB AI/A | YIELD FROM: | NUMBER OF PLANTS | <14 | 14-18 | 18-22 | 22-26 | >26 | TOTAL NO. | % CHANGE | AVE. STEM LENGTH INCHES | AVE. NO. STEMS PER PLANT |
|---|---|---|---|---|---|---|---|---|---|---|---|
| 4.0 LB | 1. HARVEST AT APPLIC. | 8 | 0 | 0 | 8 | 18 | 24 | 50 | — | 25.4 | 6.2 |
| | 2. NEXT HARVEST | 8 | 2 | 18 | 28 | 16 | 2 | 66 | +32.0 | 19.4 | 8.2 |
| | CHANGE IN CONTROL YIELD: −21.0 | | | | | | | | | | |
| 8.0 LB | 1. HARVEST AT APPLIC. | 8 | 0 | 0 | 2 | 14 | 20 | 36 | — | 26.2 | 4.5 |
| | 2. NEXT HARVEST | 8 | 4 | 16 | 24 | 16 | 2 | 62 | +72.2 | 19.2 | 7.8 |
| | CHANGE IN CONTROL YIELD: −21.0 | | | | | | | | | | |
| 16.0 LB | 1. HARVEST AT APPLIC. | 8 | 0 | 0 | 2 | 4 | 26 | 32 | — | 28.5 | 4.0 |
| | 2. NEXT HARVEST | 8 | 2 | 20 | 38 | 6 | 2 | 68 | +112.5 | 18.4 | 8.5 |
| | CHANGE IN CONTROL YIELD: −21.0 | | | | | | | | | | |
| CONTROL | 1st HARVEST | 8 | 0 | 0 | 2 | 7 | 29 | 38 | — | 27.0 | 4.8 |
| | 2nd HARVEST | 8 | 0 | 1 | 4 | 10 | 15 | 30 | −21.0 | 24.9 | 3.8 |

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

I claim:

1. A compound 1-(3-chloro-4- methyl-phthalimido)-cyclohexanecarboxamide.

2. A composition for regulating the growth of a hybrid tea rose plant which comprises an effective growth regulating amount of a compound 1-(3-chloro-4-methyl-phthalimido)-cyclohexanecarboxamide and an inert carrier.

3. The composition according to claim 2, wherein the inert carrier is a solid or a liquid.

* * * * *